(12) United States Patent
Carlson, Jr. et al.

(10) Patent No.: US 6,939,444 B2
(45) Date of Patent: Sep. 6, 2005

(54) SULFUR-BEARING RESIDUE TREATMENT SYSTEM

(75) Inventors: Curtis Instad Carlson, Jr., Houston, TX (US); Michael Stanley DeCourcy, Houston, TX (US); Jamie Jerrick John Juliette, Houston, TX (US); Thomas Albert Kaminski, Houston, TX (US); Nicole Rendon Koegel, Houston, TX (US); Nelson Ivan Quiros, Princeton Junction, NJ (US); Paul Benjamin Schladenhauffen, Houston, TX (US); Peter John Schmeidler, Delran, NJ (US); Robert R. Maven, Newtown, PA (US); William Harry Engle, Jr., Langhorne, PA (US); Arthur Meisch, Princeton Junction, NJ (US)

(73) Assignee: Rohm and Haas Company, Philadelphia, PA (US)

( * ) Notice: Subject to any disclaimer, the term of this patent is extended or adjusted under 35 U.S.C. 154(b) by 422 days.

(21) Appl. No.: 10/165,070

(22) Filed: Jun. 7, 2002

(65) Prior Publication Data

US 2002/0192132 A1 Dec. 19, 2002

Related U.S. Application Data

(60) Provisional application No. 60/298,251, filed on Jun. 14, 2001.

(51) Int. Cl.$^7$ .............................. B01D 3/06; B01D 3/38
(52) U.S. Cl. ...................... 203/88; 159/2.1; 159/47.3; 159/DIG. 26; 95/19; 95/266; 203/23; 203/38; 203/93; 203/94; 203/97; 203/98; 203/100; 422/21; 422/39

(58) Field of Search .............................. 203/2, 88, 100, 203/23, 63, 38, DIG. 8, 91–98; 159/2.1, 47.3, DIG. 32, DIG. 26; 422/21, 39; 95/266, 19

(56) References Cited

U.S. PATENT DOCUMENTS

| 3,119,764 A | * | 1/1964 | Cabbage ................. 208/208 R |
| 3,179,586 A | * | 4/1965 | Honerkamp ............ 208/216 R |
| 3,187,066 A | * | 6/1965 | Nathan ........................ 585/719 |
| 3,498,887 A | * | 3/1970 | Politte et al. ................. 203/21 |
| 3,537,977 A | * | 11/1970 | Smith, Jr. ..................... 208/89 |
| 4,555,310 A | * | 11/1985 | Marrelli ....................... 203/10 |
| 5,192,453 A | | 3/1993 | Keckler et al. |

FOREIGN PATENT DOCUMENTS

| DE | 3714016 A1 | 11/1988 | ............ C10K/1/10 |
| EP | 0 250 794 | * 7/1988 | |
| FR | 2765809 A | 1/1999 | ............ B01D/3/38 |

OTHER PUBLICATIONS

Kirk–Othmer Encyclopedia of Chemical Technology, "Methacrylic Acid and Derivatives—6. Manufacture and Processing", John Wiley & Sons, Inc. (1995).

* cited by examiner

Primary Examiner—Glenn A. Caldarola
(74) Attorney, Agent, or Firm—Marcella M. Bodner; Alan Holler

(57) ABSTRACT

A sulfur-bearing residue treatment system is provided for the recovery of valuable organic components and the reduction of capital costs and operating costs. The treatment system involves the use of a stripping vessel in conjunction with a heating apparatus. All elements of the treatment system may be coupled together to form one integral piece of equipment.

22 Claims, 3 Drawing Sheets

SULFUR-BEARING RESIDUE TREATMENT SYSTEM

CROSS REFERENCE TO RELATED PATENT APPLICATION

This is a non-provisional application of prior pending U.S. provisional application Ser. No. 60/298,251 filed on Jun. 14, 2001.

The present invention relates in general to the field of residue treatment in industrial manufacturing operations, and more particularly, to an improved optionally integrated residue treatment system used to treat sulfur-bearing residue streams for the recovery of valuable organic components. Capital and operating costs are significantly reduced as a result of the improved process.

In various large-scale industrial manufacturing operations, sulfur-bearing residue streams are created as a by-product of the manufacturing process. Such sulfur-bearing residue streams are produced in several processes, including, but not limited to, the manufacture of (meth) acrylic acid and its esters, (meth)acrylonitrile, hydrogen cyanide, caprolactam, tertiary alkyl amines, petroleum refining operations, steel production and power plant operations. These sulfur-bearing residue streams often contain valuable organic components.

It is desirable to recover these organic components to increase overall yield for the process. It is particularly desirable as the large scale industrial manufacturing market is extremely cost-sensitive and any improvement in process yield, however slight, can result in significant cost advantages for the manufacturer. Additionally, it is desirable to remove as much water as possible from the residue stream to minimize the amount of remaining residue that must be disposed of or processed in a downstream operation. Another goal is to purify the residue so it is more amenable to disposal.

A conventional sulfur-bearing residue stream treatment system is either a batch or continuous process wherein a single stripping vessel containing the residue stream is contacted or heated with only live steam to volatilize and then remove organic components and water from the residue stream. The term "live steam," as used herein, means steam that is sparged directly into a vessel wherein the steam directly contacts the process stream. Once the organics are removed from the residue stream, they can be flared, condensed or recycled back into the process. If recycled, additional complicated equipment and significant capital costs are usually involved. The remainder of the residue, minus the recovered organics, is a concentrated sulfur-bearing residue stream that may be either disposed of or processed, for example, in an acid regeneration or ammonium sulfate production process. If routed to an acid regeneration operation, the concentrated residue may be incinerated in a furnace to recover sulfur values to ultimately form compounds such as sulfuric acid.

There are many problems associated with conventional live steam sulfur-bearing residue stream treatment processes. First, when using live steam as the heat source in the treatment process, it is impossible to concentrate the residue to an optimum level as water is continually added to the residue stream via the live steam. Specifically, adding live steam results in the volatilization of most of the organics, but also results in condensation of some of the live steam into the stream. Thus, the residue stream is less concentrated in organics but more concentrated in water. This is disadvantageous to downstream processors because the larger volume of water in the stripped residue must be processed or disposed of. A larger volume of water in the stripped residue in an acid regeneration or ammonium sulfate production process means that larger equipment and more energy must be used to incinerate or concentrate the residue. In fact, to achieve optimum dehydration of the residue, additional secondary removal steps may be necessary, which are in and of themselves, very expensive.

Another pitfall of conventional live steam treatment systems is that operating temperatures for the process are limited. High temperatures are necessary for optimum organic recovery. But high temperatures cannot be achieved with conventional live steam systems because for a given operating pressure, the addition of water to the residue stream limits the equilibrium boiling point, and thereby limits the temperature of the system. Because the maximum temperature the system can reach is limited, the amount of valuable organics and water that can be removed from the system is severely limited. This leads to losses in overall yield.

Another disadvantage associated with live steam treatment systems is that they foul easily, causing down-time and clean-up costs to be significant. Live steam may polymerize components in the residue stream, thereby forming intractable solids, which are very difficult and costly to remove. This tendency to foul also makes handling and pumping the residue extremely difficult.

Yet another problem associated with conventional live steam treatment operations is that the sparger, which introduces the live steam into the stripping vessel, has a tendency to be corroded by the highly corrosive sulfur-bearing residue stream and live steam mixture. Other pieces of equipment also tend to corrode including the lining of the stripping vessels. Replacement is expensive, and the down-time associated with replacement is costly.

Additionally, manufacturers have suffered other losses in overall yield as they have not been able to recover valuable organic components from sulfur-bearing and non-sulfur-bearing waste streams that are usually disposed of. The term "waste stream" as used herein means a nonproduct stream formed in the chemical processing operation that contains water, organics, and/or polymer, and may be in vapor or liquid form.

For example, in a methyl methacrylate ("MMA") process, a liquid waste stream that is referred to as the "rag stream", is typically disposed of, leading to losses in overall yield. The term "rag stream" as used herein refers to one or more polymer containing waste streams formed in the separation or purification steps in an MMA process. The rag stream comprises valuable organic components including for example, polymethyl methacrylate, methacrylic acid ("MAA"), MMA, methanol, and other valuable organics that heretofore have been ignored by conventional residue treatment systems. These organics have been ignored in waste streams such as the MMA rag stream because they are typically difficult to process and generally have a fundamental tendency to foul. Consequently, the organics in these waste streams are lost in a conventional process and overall yield suffers.

In sum, conventional live steam treatment systems for sulfur-bearing residue treatment are problematic to manufacturers as they increase capital costs, operating costs and yield losses significantly.

Accordingly, there is a need for an effective, low operating cost and low capital cost method of treating sulfur-bearing residue streams so that an optimal amount of valuable organics and water are removed from the streams.

In a first embodiment of the present invention, improved sulfur-bearing residue treatment processes are provided that perform the functions of recovering valuable organic components from the residue stream and concentrating the remaining residue stream to such a level that overall yield and cost savings are increased. In a second embodiment of the present invention, all of the elements of the residue treatment system are coupled to provide one integral piece of equipment wherein tremendous cost savings are achieved as less piping and other peripheral equipment are needed.

Thus, in a first aspect of the first embodiment of the present invention, there is provided a process for stripping organics from a sulfur-bearing residue stream comprising:

(a) conveying a liquid, organics-containing, sulfur-bearing residue stream to a stripping zone; and (b) in the stripping zone, indirectly heating the liquid, organics-containing, sulfur-bearing residue stream to form a vapor stream containing organics and a liquid residue stream.

In a second aspect of the first embodiment of the present invention, there is provided a process for stripping organics from a sulfur-bearing residue stream comprising:

(a) conveying a liquid, organics-containing, sulfur-bearing residue stream to a stripping zone;

(b) separating the liquid, organics-containing, sulfur-bearing residue stream, in the stripping zone, into a vapor stream containing organics and a liquid residue stream;

(c) conveying the liquid residue stream to a lower flash zone; and (d) indirectly heating the contents of the lower flash zone to flash vaporize the contents of the lower flash zone into a lower flash zone vapor stream and a lower flash zone liquid residue stream.

In a third aspect of the first embodiment of the present invention, there is provided a process for stripping organics from a sulfur-bearing residue stream comprising:

(a) conveying a liquid, organics-containing, sulfur-bearing residue stream to a stripping zone;

(b) in the stripping zone, separating the liquid, organics-containing, sulfur-bearing residue stream into a vapor stream containing organics and a liquid residue stream;

(c) conveying the liquid residue stream to a lower flash zone;

(d) in the lower flash zone, flash vaporizing the liquid residue stream into a lower flash zone vapor stream and a lower flash zone residue stream;

(e) withdrawing the lower flash zone liquid residue stream from the lower flash zone and separating the lower flash zone liquid residue stream into a first portion and a second portion; and (f) indirectly heating the first portion of the lower flash zone liquid residue stream and returning the heated first portion of the lower flash zone liquid residue stream to the lower flash zone.

In a first aspect of the second embodiment of the present invention, there is provided a sulfur-bearing residue treatment apparatus comprising:

a substantially cylindrical residue treatment system having an upper flash tank section, a stripping vessel section, a lower flash tank section, an upper transition section fluidically connecting the upper flash tank section and the stripping vessel section, and a lower transition section fluidically connecting the stripping vessel section and the lower flash tank section; the upper flash tank section having a diameter different from that of the stripping vessel section; the lower flash tank section having a diameter different from that of the stripping vessel section;

an indirect heater, operatively connected to the lower flash tank section;

a liquid inlet port in the upper flash tank section;

a vapor exit port in the upper flash tank section; and a liquid exit port in the lower flash tank section.

In a second aspect of the second embodiment of the present invention, there is provided a sulfur-bearing residue treatment apparatus comprising;

a substantially cylindrical residue treatment system having an upper flash tank section, a stripping vessel section, a lower flash tank section, an upper transition section fluidically connecting the upper flash tank section and the stripping vessel section, and a lower transition section fluidically connecting the stripping vessel section and the lower flash tank section; the upper flash tank section having a diameter different from that of the stripping vessel section; the lower flash tank section having a diameter different from that of the stripping vessel section;

a liquid inlet port in the upper flash tank section;

a vapor exit port in the upper flash tank section;

a liquid exit port in the lower flash tank section;

a return port in the lower flash tank section; and an indirect heater, connected between the liquid exit port in the lower flash tank section and the return port in the lower flash tank section.

As will be appreciated by those skilled in the art after reading this disclosure, one advantage of the invention described herein is that an optimum amount of organics can be removed from the sulfur-bearing residue stream. Organic recovery is improved by the present invention through, inter alia, realized higher temperatures. This provides for increased overall yield from the manufacturing process. Due to the cost-sensitive nature of the industrial manufacturing market, this increase in yield can result in significant cost advantages for the manufacturer.

Another advantage of the present invention is that water is not added to the sulfur-bearing residue stream via a live steaming process. Therefore, more water can be removed from the sulfur-bearing residue overall, reducing the volume of concentrated residue that must be disposed of or processed. Thus, less water must be burned and heated with a furnace prior to processing in an acid regeneration unit, or removed in an ammonium sulfate unit. Downstream equipment can, therefore, be smaller and less energy must be used to treat the residue. Significant capital costs and operating cost reductions may be realized by the end-use processor.

An additional advantage of the present invention is that the system is more resistant to fouling. Therefore, additional downtime and clean-up costs can be avoided. Further, the equipment used in the present invention is resistant to corrosion. The manufacturer can thereby avoid spills, environmental contamination, and the additional cost of replacing the equipment.

Yet another advantage of the residue treatment system of the present invention is that it allows less volatile organic components in the residue stream to be converted to more volatile components that are more easily removed from the stream. Overall yield is increased and the manufacturer realizes an additional cost advantage. Also, the present invention provides for a method to recover valuable organics from waste streams such as the MMA rag stream by processing it with the sulfur-bearing residue stream in the residue treatment system. This has heretofore been unknown.

A more complete understanding of the present invention and advantages thereof may be acquired by referring to the following description taken in conjunction with the accompanying drawings, in which like reference numbers indicate like features, and wherein.

The sulfur-bearing residue treatment system and its method of use described herein involve the treatment of sulfur-bearing residues for the recovery of valuable organics and for concentration prior to further downstream processing. It may be used to treat sulfur-bearing residues created in one process or many processes. Typically, industrial manufacturers need to dispose of these residue streams while at the same time recovering all useable and valuable components from the residue stream to increase overall process yield and to minimize any remaining residue that must be disposed of or processed downstream. As the industrial manufacturing market is very cost-sensitive, manufacturers must be able to accomplish these things with minimal operating costs and capital costs. The invention described herein satisfies these goals.

Figure 1:
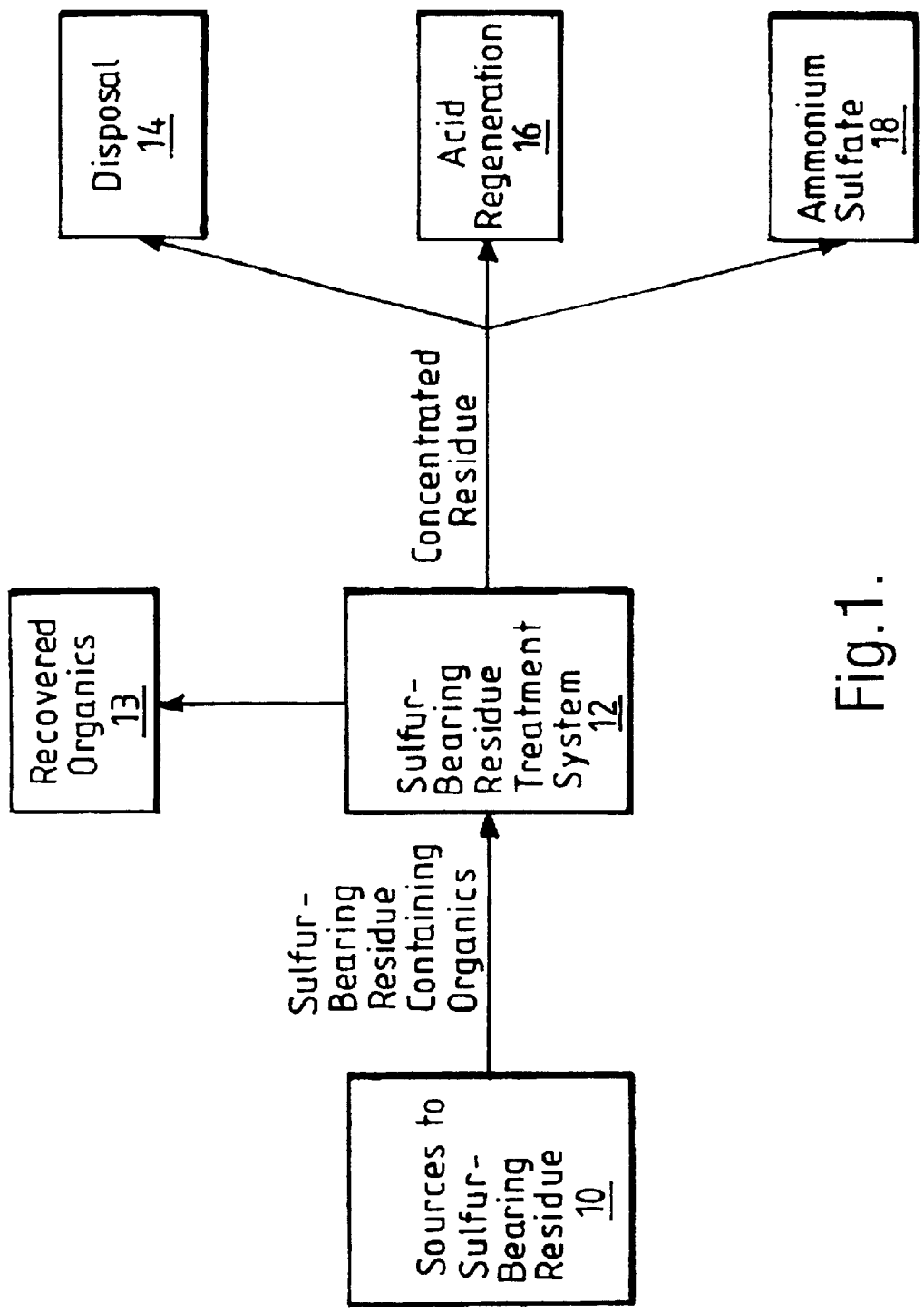
FIG. 1 is an example of a process flow diagram depicting the overall processing steps described herein.

Shown in FIG. 1 is one example of a typical process flow diagram of a sulfur-bearing residue stream illustrating possible origins and downstream processes for the sulfur-bearing residue stream. The sulfur-bearing residue stream can be derived from many sources 10 including but not limited to the manufacture of (meth)acrylic acid and its esters, acrylonitrile, methacrylonitrile, hydrogen cyanide, and caprolactam, tertiary alkyl amine, and also petroleum refining operations, steel production, and power plant operations. All of these sources are contemplated within sources 10. Any sulfur-bearing residue stream that is generated by sources 10 may include components such as water, sulfuric acid, ammonium bisulfate, ammonium sulfate, methanol, MMA, MAA, methane sulfonic acid and other trace components, for instance, hydrogen sulfide, acrylonitriles, benzene, and hydrogen cyanide.

In the embodiment of the treatment process illustrated in FIG. 1, the sulfur-bearing residue stream is subjected to treatment system 12, wherein valuable organic components and water are stripped from the sulfur-bearing residue. Valuable organic components, in addition to water, are recovered at 13. An additional separation of the water and the organics can be performed. Thereafter, the organics may be condensed, flared or recycled back to the manufacturing process. The remaining residue, minus the recovered organic components, can then be subjected to further processing, such as acid regeneration 16 and ammonium sulfate production 18 or disposal 14, or it may be recycled back into the residue treatment process.

Figure 2:
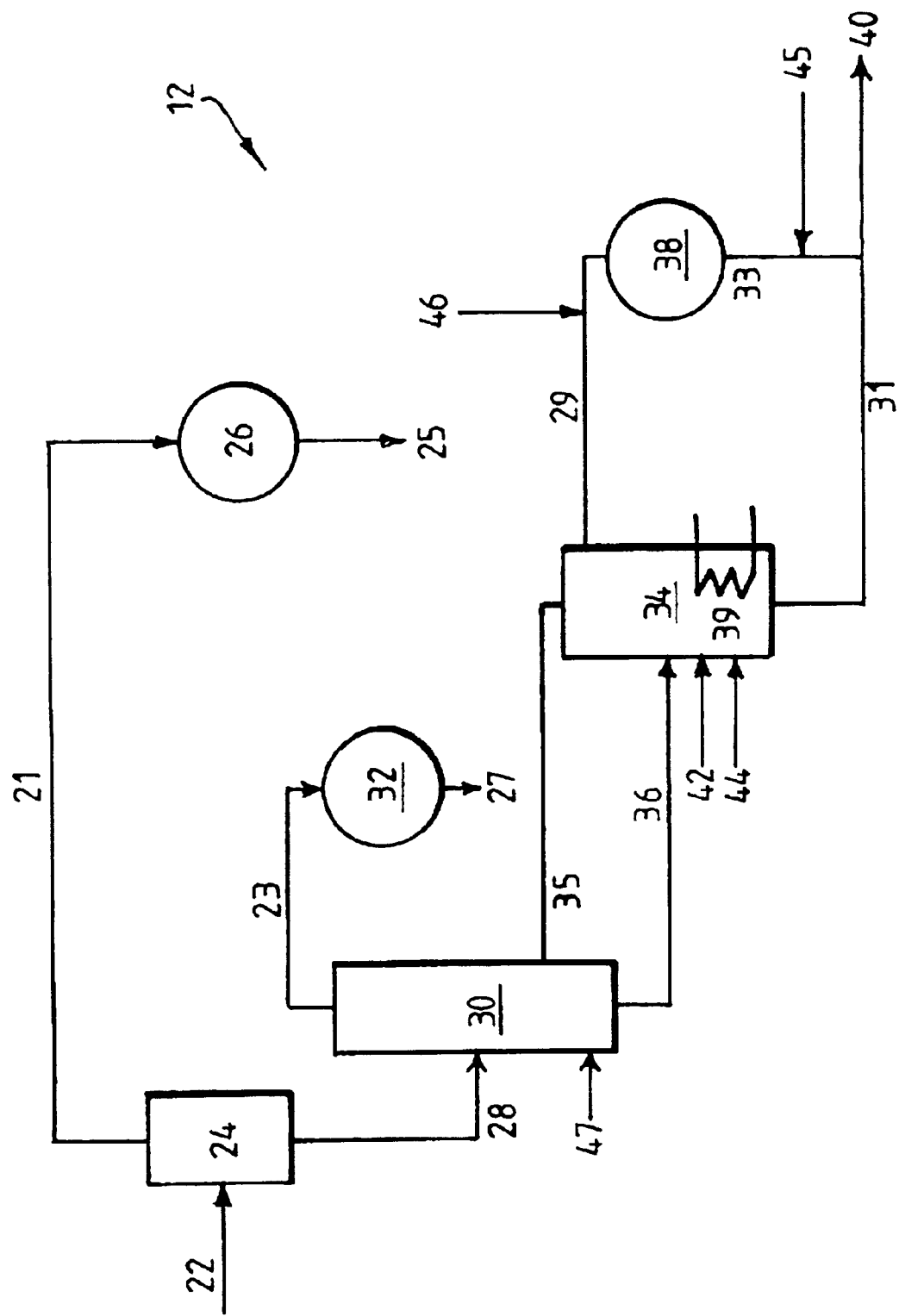
FIG. 2 is a diagram of one embodiment of the improved sulfur-bearing residue treatment system of the present invention displaying certain elements of the system.

FIG. 2 depicts an embodiment of the specific sulfur-bearing residue treatment system 12 illustrated in FIG. 1, further comprising an upper flash tank and a lower flash tank. As shown in FIGS. 1 and 2, a sulfur-bearing upper flash tank feedstream, which contains organics and water, is generated by sources 10. This upper flash tank feedstream can be conveyed through conduit 22 into optional upper flash tank 24. The pressure in upper flash tank 24 is typically lower than the pressure of the sulfur-bearing upper flash tank feedstream. Under these circumstances, a flash occurs in the upper flash tank 24 creating a separation forming an overhead organics and water stream. The valuable organics in the overhead organics and water stream are taken overhead to condenser 26. Condenser 26 may be a single condenser or may be more than one condenser run in parallel or in series. Organics in the overhead organics and water stream may include methanol, MMA, MAA and other components. Inhibitors may be added to condenser 26. Upper flash tank 24 further may contain internal components that aid this separation of vapors and liquids in the residue streams. Examples of such internal components include trays, baffles and packing.

The sulfur-bearing residue stream that has not been flashed off in upper flash tank 24 is then conveyed through conduit 28 into stripping vessel 30. Stripping vessel 30 may be a column, kettle, tank, a pressurized vessel or a vessel operated under vacuum pressure. Typically, stripping vessel 30 is operated at a pressure not greater than atmospheric; it being preferable to operate stripping vessel 30 at as low a pressure as possible. Regardless of the particular type of vessel utilized for stripping vessel 30, in certain specific embodiments, stripping vessel 30 can contain at least one internal component of the sort described herein.

In stripping vessel 30, a separation occurs forming a stripping vessel vapor stream containing organics and water and a stripping vessel residue stream. The stripping vessel vapor stream containing organics and water is taken overhead to condenser 32 to recover organics.

Condenser 32 may also be a single condenser or more than one condenser placed in series or parallel. The stripping vessel residue stream, which typically does not contain a substantial amount of recovered organic components, exits stripping vessel 30 and may be conveyed to lower flash tank 34 through conduit 36. Since sulfuric acid forms a catalytic environment at high temperatures; lower flash tank 34 can be useful following stripping vessel 30 as it is a vessel wherein desirable chemical reactions may occur within this catalytic environment forming useful and more easily removed organic components.

For example, in an MMA process, components such as methanol and MAA in the stripping vessel residue stream may react to form MMA, a more volatile, and consequently, a more easily removed component.

Indirect heaters such as heat exchangers are used as the heat source for the residue treatment system of the present invention rather than only live steam so that optimum concentration of the remaining residue can be achieved. (By indirect heating is meant the heating of a "cold" material where there is no mixing of the "cold" material with a "hot" material to form a mixture of what had been some or all of the "cold" material and what had been some or all of the "hot" material, the terms "cold" and "hot" being used in a relative sense. Examples of indirect heating include passage through a heat exchanger, e.g., a shell and tube heat exchanger, and irradiation, e.g., irradiation with microwave energy.) Indirect heaters may be internal (heater 39) or external (heater 38) to flash tank 34. If the heating apparatus is a heat exchanger, it may include a heat source and heat transfer surfaces, such as heat exchange tubes. The heated stripping vessel residue stream is separated in lower flash tank 34 into a lower flash tank vapor stream and a lower flash tank residue stream.

The lower flash tank residue stream is optimally concentrated and exits residue treatment system 12 (FIG. 1) at conduit 40 for disposal or for further processing in acid regeneration, ammonium sulfate production and/or other recovery operations. Additionally, in another embodiment of the present invention, the lower flash tank residue stream may be conveyed by conduit 40 to another vessel operated under a reduced pressure as compared to the lower flash tank for further concentration.

Figure 3:
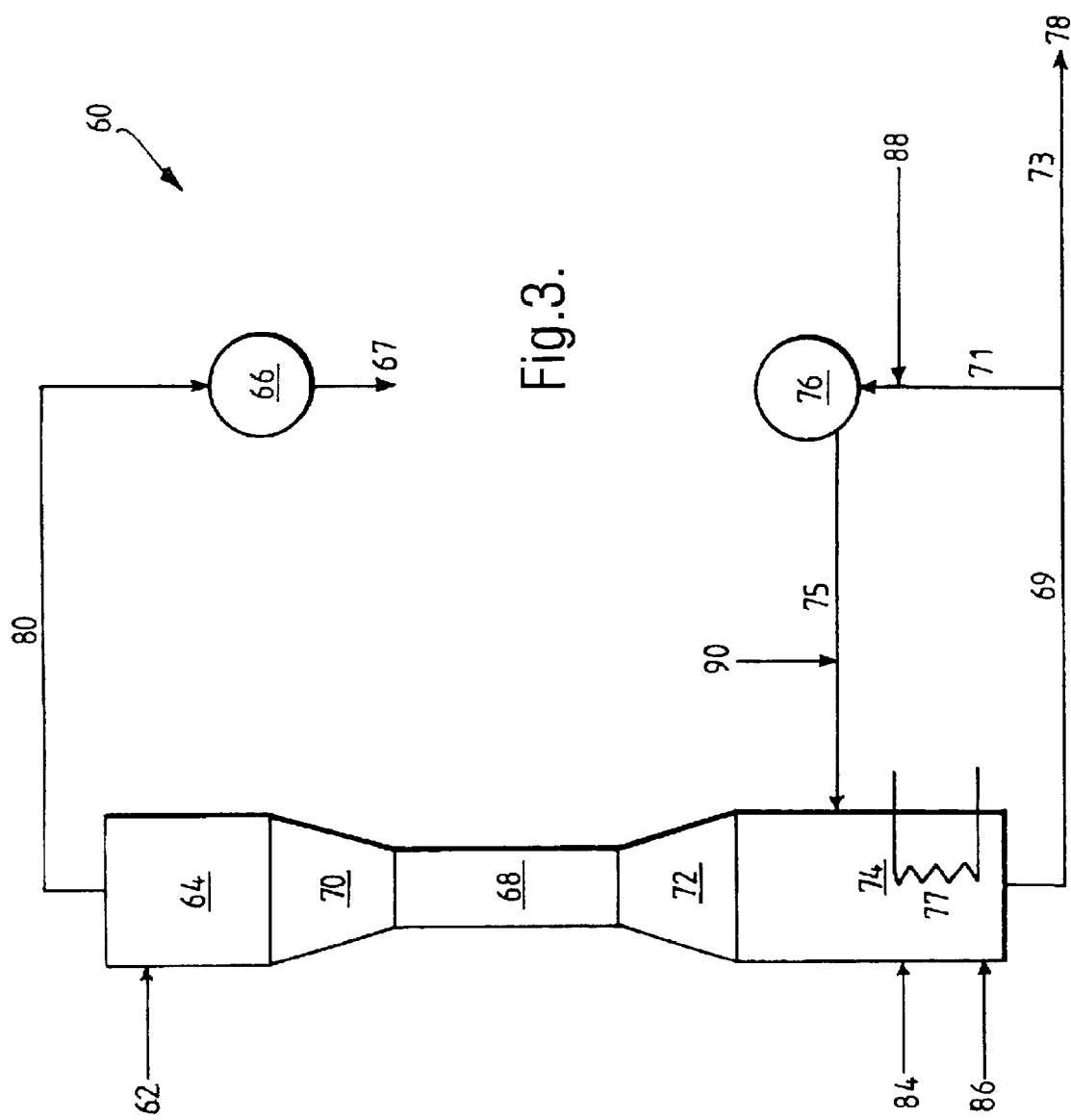
FIG. 3 is a diagram of another embodiment of the improved sulfur-bearing residue treatment system of the present invention, wherein the individual elements of the system are coupled to comprise an integral piece of equipment.

FIG. 3 is an alternative embodiment of the residue treatment system of the present invention shown generally at 60. In this alternative embodiment, all elements of the residue treatment system are coupled to form one integral piece of equipment. Here, a sulfur-bearing residue stream containing organics is introduced into the residue treatment system through conduit 62 into upper flash tank section 64. Upper flash tank section 64 is fluidically connected to stripping vessel section 68 via upper transition section 70. Upper flash tank section 64 may contain internal components such as trays, baffles, and packing to aid in the separation of the gas phase and the liquid phase from the upper flash tank feed stream. Some organics are removed from the upper flash tank feed stream in upper flash tank section 64 and may be carried overhead to condenser 66 via conduit 80. Upper transition section 70 serves as a connector between upper flash tank section 64 and stripping vessel section 68. Upper transition section 70 also allows the vapor from upper flash tank section 64 and the vapor from stripping vessel section 68 to combine, which is beneficial for separation. Upper transition section 70 also facilitates the flow of liquid components to stripping vessel section 68 from upper flash tank section 64. Another separation occurs within the sulfur-bearing residue stream in stripping vessel section 68. Lower transition section 72 fluidically connects stripping vessel section 68 and lower flash tank section 74. Lower flash tank section 74 also provides a residence time that induces or enhances the reactions that occur within the remaining residue stream to form more easily removed and commercially valuable organic components. All stripped organic components in this embodiment of the present invention are withdrawn to condenser 66 through conduit 80. The lower flash tank residue stream exits the residue treatment system 60 at conduit 78 and proceeds to other end processes such as acid regeneration, ammonium sulfate production, or to disposal, as described above with respect to FIG. 1. In another embodiment, the lower flash tank residue stream may be conveyed to another vessel (not shown) operated under a reduced pressure as compared to that of the lower flash tank for further concentration. Heat exchanger 76 is disposed between the liquid exit port in the lower flash tank zone via conduit 71 and the return port in the lower flash tank, as represented by conduit 75, and is used as the heat source for this alternative embodiment of the present invention. Alternatively, a heat exchanger 77 may be internal to lower flash tank section 74. Because the upper flash tank section and the lower flash tank section in this alternative embodiment are coupled to stripping vessel section 68, the manufacturer realizes a tremendous cost savings as less piping and other peripheral equipment are needed.

All elements of the present invention should be resistant to the corrosive effects of the sulfur-bearing residue stream. Under these circumstances, such elements that come into contact with the sulfur-bearing residue stream may be constructed of or lined with glass, epoxy, resins, refractory, or metals that are resistant to the corrosive effects of the residue stream. Zirconium, hafnium, titanium, tantalum, molybdenum, nickel, chromium, copper, and alloys comprising one or more of these metals are particularly useful in the present invention. The equipment that comes into contact with the sulfur-bearing residue stream is preferably comprised of zirconium. Heat-treated-zirconium equipment, wherein the welds of the zirconium are heat-treated, is most preferred. Such corrosion resistant materials must be able to withstand processing temperatures of 100° C. to 200° C. in corrosive environments. Additionally, certain desired vapor lines may be comprised of copper.

In the present invention, the sulfur-bearing residue stream can be heated by means other than direct/live steam addition as used in conventional processes. Heating of the residue in this manner enables the system to achieve higher temperatures for optimum organic recovery. This increases the overall yield of the process. Further, when live steam is used as the heat source for a conventional residue treatment system, steam ultimately condenses within the system, increasing the overall volume of water within the residue. By using heat sources other than live steam, as disclosed in the present invention, additional water volume is not put into the system and the residue can be optimally concentrated. This results in a cost savings in downstream processing operations.

In one embodiment of the present invention, the sulfur-bearing residue stream may be indirectly heated as shown in FIG. 2 by passing it through a heating apparatus such as an external heat exchanger, for instance a shell and tube exchanger, a spiral exchanger, or a plate and frame exchanger, wherein heat is supplied using a transfer media, such as hot oil or steam. If an external shell and tube heat exchanger are used, it is preferred that the residue pass through the tubeside and the transfer fluid pass through the shell side of the exchanger.

The sulfur-bearing residue stream may be pumped through the exchanger or, alternatively, allowed to circulate through thermosiphon action. Also, because the sulfur-bearing residue stream comes into direct contact with the heat transfer surfaces of the exchanger, it is necessary to construct the exchanger from corrosion resistant materials, for example, zirconium, titanium, tantalum, molybdenum, hafnium, glass, ceramic, epoxy, resins and the like. If steam is used as the heat transfer media, it should be desuperheated to prolong the life of the heat exchange equipment. This will result in a cost savings for the manufacturer.

In an alternative embodiment, one or more heating coils 39 may be installed on or in the interior of lower flash tank 34 to form an internal exchanger; in such an arrangement, heat is supplied by flowing a heat transfer media, such as hot oil or steam, through one or more coils. If an internal exchanger is utilized, a bayonet type heat exchanger is preferred as it can be easily removed, for example, to perform maintenance and inspection. Because the sulfur-bearing residue stream typically comes into direct contact with the heat transfer surfaces of the exchanger, it is often preferable to construct the exchanger from corrosion resistant materials, e.g., zirconium, titanium, tantalum, molybdenum, hafnium, glass, ceramic, epoxy, resins and the like. If steam is used as the heat transfer media, it should be desuperheated to prolong the life of the heat exchange equipment. This will result in a cost savings for the manufacturer.

Heating apparatus 38 (FIG. 2) and heating apparatus 76 (FIG. 3) can also include external, direct-fired exchangers wherein combustion of a fuel is the source of heat, rather than a transfer medium. These would be economically advantageous in situations where significant waste streams that may be utilized as fuels are readily available. Similarly, waste heat exchanger apparatus wherein the heat transfer media is a hot waste gas, such as the effluent of an incinerator or a sulfuric acid regeneration furnace, may be utilized to heat the sulfur-bearing residue in accordance with the present invention.

In still another embodiment, heat energy is supplied in the form of microwave radiation directed into the lower flash tank vessel. Such an embodiment is advantageous in that no exchanger is used at all, significantly reducing the capital cost of the residue concentration system. In this embodiment, a microwave generator is located external to the lower flash tank and microwave energy is directed via a waveguide through a high-purity quartz window (for example, a sightglass) into the closed flash tank. An optional applicator may also be used inside the flash tank to improve energy distribution. Such microwave generation systems are available from Communications & Power Industries of Palo Alto, Calif. Microwave frequencies of 2.45 gigahertz and 915.0 megahertz are especially preferred due to their strong preferential heating of water. In this embodiment, it is preferred that the lower flash tank apparatus be lined with a material that is not readily heated by the particular frequency of microwave energy used. Refractory ceramics comprising alumina or silica are especially preferred.

In certain preferred embodiments, the flash tanks that are used should be constructed of, or lined with, a corrosion resistant material as described above due to the corrosive nature of the environment. One example of a particularly preferred material is heat treated zirconium as described above. Such material should be able to withstand temperatures of 100° C. to 200° C. and pressures from below atmospheric to 5 atmospheres in an acidic environment.

Flash tanks used in the present invention also may contain internal components to facilitate the separation of the vapor phase and the liquid phase in the incoming sulfur-bearing residue stream. Such internal components may include trays, packing materials, distributors, additional feed nozzles and the like, and/or any combination thereof.

All condensers used in corrosive environments should also preferably be constructed of corrosion resistant materials as described above. Condensers 26 and 32 (FIG. 2) and condenser 66 (FIG. 3) may be a single vessel or more than one vessel arranged in series or in parallel. If more than one vessel is arranged in series, the vessels following the first condensing vessel may not need to be made from a corrosion resistant material. The acidic components and the potentially corrosive organic components in the stream, by the time it reaches the consecutive condensing vessel or vessels, may have been diluted enough to not pose as great of a corrosion hazard. Thus, any vessels following the first condensing vessel when placed in series may be formed from less exotic materials such as stainless steel. However, if desired, all condensing vessels may be made from or lined with corrosion resistant materials.

Additionally, inhibitors may be used in the condensers to prevent polymerization of the components in the organic stream. Polymerization inhibitors are especially useful to prevent polymerization both during the process of preparing of (meth)acrylates and during storage and shipment of (meth)acrylates.

The polymerization inhibitor may include a water soluble or alcohol soluble polymerization inhibitor. Suitable examples include but are not limited to, hydroquinone; 4-methoxyphenol; 4-ethoxyphenol; 4-propoxyphenol; 4-butoxyphenol; 4-heptoxyphenol; hydroquinone monobenzylether; 1,2-dihydroxybenzene; 2-methoxyphenol; 2,5-dichlorohydroquinone; 2,5-di-tert-butylhydroquinone; 2-acetylhydroquinone; hydroquinone monobenzoate; 1,4-dimercaptobenzene; 1,2-dimercaptobenzene; 2,3,5trimethylhydroquinone; 4-aminophenol; 2-aminophenol; 2-N,N-dimethylaminophenol; 2-mercaptophenol; 4-mercaptophenol; catechol; monobutylether; 4-ethylaminophenol; 2,3-dihydroxyacetophenone; pyrogallol; 1,2-dimethylether; 2-methylthiophenol; t-butyl catechol; di-tert-butylnitroxide; di-tert-amylnitroxide; 2,2,6,6-tetramethyl-piperidinyloxy; 4-hydroxy2,2,6,6-tetramethyl-piperidinylox 4-oxo-2,2,6,6-tetramethyl-piperidinyloxy; 4-dimethylamino 2,2,6,6-tetramethyl-piperidinyloxy; 4-amino-2,2,6,6-tetramethyl-piperidinyloxy; 4-ethanoloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pyrrolinyl-1-oxy-3-carboxylic acid; 2,2,3,3,5,5,6,6-octamethyl-1,4-diazacyclohexyl-1,4-dioxy; salts of 4-nitrosophenolate; 2-nitrosophenol, 4-nitrosophenol, copper compounds such as copper dimethyldithiocarbamate; copper diethyldithiocarbamate; copper dibutyldithiocarbamate; copper salicylate; methylene blue; iron; phenothiazine; 3-oxophenothiazine, 5-oxophenothiazine, phenothiazine dimer, 1,4-benzenediamine, N-(1,4-dimethylpentyl)-N'-phenyl; 1,4-benzenediamine, N-(1,3dimethylbutyl) -N'-phenyl; isomers thereof; mixtures of two or more thereof; or mixtures of one or more of the above with molecular oxygen.

The polymerization inhibitor is typically used at levels ranging from 100 ppm to 4,000 ppm by weight. The inhibitor(s) may be added as is or may be combined with a suitable diluent. Use of an inhibitor in the condensers generally enhances the reliability of the condensers.

One advantage obtained from using a lower flash tank apparatus in the sulfur-bearing residue treatment system of the present invention is that desirable chemical reactions can occur within the inherently catalytic stripping vessel residue stream that enhance the recovery of organics. For instance, in the production of MMA, methanol and MAA in the stripping vessel residue stream may react to form MMA in the lower flash tank. MMA is a lighter organic component and more easily removed from the residue. This increases the overall yield of the process, especially because, as in the example, the reacted compound, here MMA, can be sold directly to customers as a valuable commodity. Allowing this reaction and others like it to occur in the lower flash tank 34 (FIG. 2) or in lower flash tank section 74 (FIG. 3) is advantageous to the manufacturer in terms of overall yield. Additionally, inlet ports can be added to the lower flash tank so that a reactant such as an alkanol, e.g., methanol, ethanol or butanol, can be added to the concentrated residue to induce desired reactions between and among the components in the concentrated residue stream similar to the one described above. Such inlet ports are shown at 42 (FIG. 2) and 84 (FIG. 3). The actual placement of such inlet ports to lower flash tank 34 or lower flash tank section 74 is not critical to the present invention. An example of when this would be used is when ethanol is added to the stripping vessel residue stream to react with acrylic acid to produce the more volatile ethyl acrylate. In the case of MMA production, for another example, methanol can be fed into the lower flash tank 34 or lower flash tank section 74 through conduit 42 or 84 respectively so that it can esterify MAA in the concentrated residue stream to form MMA. Reactions such as these are enhanced by the inherent catalytic environment of the sulfur-bearing concentrated residue.

In another embodiment of the present invention, another feed nozzle may be added to the stripping vessel for the purpose of feeding a waste stream comprising ammonia to the stripping vessel to be scrubbed by the sulfur-bearing residue stream.

In an additional embodiment of the present invention, the upper flash tank section may have nozzles oriented in a manner such that the fluid spins around the circumference of the vessel, which enhances the separation of the vapor phase from the liquid phase in the incoming upper flash tank feed stream. These are referred to herein as tangential entry nozzles. If tangential entry nozzles are used in the upper flash tank section in an embodiment such as the one depicted in FIG. 3, it is preferred that baffles be used in upper transition section 70 to stop the spinning of the liquid before it reaches stripping vessel section 68.

Although internal packing mechanisms or trays may be used in stripping vessel 30 (FIG. 2) and stripping vessel section 68 (FIG. 3), in the present invention it has been found that such packing or trays are not necessary to achieve enhanced recovery of organics. However, it should be noted that use of such trays or packing is contemplated within the present invention. Because water is typically not added to the sulfur-bearing residue stream as it would be in a conventional live steam-based system, the need for trays and other packing inside the stripping vessel is reduced.

In a steam-based system, the trays and other packing enhance the steam-to-liquid contact that drives the stripping process. In the heating apparatus treatment system of the present invention, the stripping process does not depend on steam to liquid contact, and therefore, trays and internal packing are not necessary in the stripping vessel.

In certain embodiments, it is preferred, to use at least one internal component inside the stripping vessel. Enhanced recovery in the heat exchanger-based treatment systems of the present invention can be achieved with a minimal number or without such internal components. By not using trays or packing within stripping vessel section 30 (FIG. 2) or stripping vessel section 68 (FIG. 3), the manufacturer realizes a substantial capital savings. This is especially true given the corrosion resistance requirements of such trays and packing and the expense of the associated materials.

By way of example and not limitation, a description of the present invention, specifically the embodiment illustrated by FIG. 2, when used in an MMA process is provided. The most common feedstock for the production of MMA is acetone cyanohydrin ("ACH"). The first stage of producing MMA from ACH involves hydrolysis where the ACH is hydrolyzed by an excess of sulfuric acid to form alpha-sulfatoisobutyramide ("SIBAM"), alpha-hydroxyisobutyramide ("HIBAM"), methacrylamide ("MAM"), and MAA. Following hydrolysis, the hydrolysis mix is cracked to form MAM and a small amount of MAA, HIBAM and SIBAM. The cracked mix is then esterified with methanol to form valuable product MMA, but a sulfur-bearing residue stream is also produced that contains water, sulfuric acid, ammonium bisulfate, methanol, MMA, MAA, methanesulfonic acid and other trace components. It is desirable to recover the valuable organics from this residue stream and to concentrate the residue so that there is less residue to handle in downstream processing or disposal operations. To accomplish these goals, this sulfur-bearing upper flash tank feedstream is fed, for example, through conduit 22 into upper flash tank 24 where some of the water and organic components including MMA, MAA, and methanol are removed from the stream and taken overhead through conduit 21 to condenser 26. The remainder of the residue, which is primarily ammonium sulfate, ammonium bisulfate, sulfuric acid, water, acetone, disulfonic acid, methanol, MAA and MMA, exits flash tank 24 and is conveyed into stripping vessel 30 via conduit 28. In stripping vessel 30, separation occurs and valuable organics components like methanol, MMA and MAA along with water are taken overhead via conduit 23 to condenser 32. From condenser 32 and condenser 26, the recovered organics and water can be recycled back into the process or stored via conduit 27 and conduit 25, respectively. From stripping vessel 30, the stripping vessel residue stream, which is primarily ammonium sulfate, ammonium bisulfate, sulfuric acid, water, acetone disulfonic acid, methanol, MAA and MMA, is fed into lower flash tank 34 by conduit 36. While the stripping vessel residue stream is residing in lower flash tank 34, methanol is added to the residue via conduit 42 to induce chemical reactions between and among components of the stripping vessel residue stream to produce lighter organic components, specifically MMA from MAA and methanol. These organic components are recovered at condenser 32 via conduit 35, stripping vessel 30 and conduit 23. The lower flash tank residue stream exits lower flash tank 34 and is fed to heat exchanger 38 via conduits 31 and 33 and then refed into lower flash tank 34 via conduit 29 after exiting the heat exchanger. Once the optimal amount of organics have been recovered, the lower flash tank residue stream, which is primarily composed of ammonium sulfate, ammonium bisulfate, sulfuric acid, water, and acetone disulfonic acid, exits the residue treatment system at conduit 40 for further processing or disposal.

Another important and advantageous aspect of the present invention is that the present invention provides for recovery of organic components in waste streams, such as the rag stream in an MMA process, by feeding it back into the treatment system. In an MMA production process, for instance, the rag stream typically comprises polymethylmethacrylate, MMA, methanol, MAA and other valuable organics. Another example of a waste stream is a railcar wash stream containing products such as MMA and water. If these organics are recovered, overall recovery is enhanced. In conventional systems, waste streams have been ignored as a source of valuable organics because they are difficult to process and have a tendency to foul easily. In fact, they are usually incinerated or disposed of off-site or on-site, resulting in inevitable overall yield losses. The present invention, however, has found that waste streams such as the MMA rag stream may be freely inserted back into the system for treatment with little fouling problems. Thus, the valuable organics in these waste streams can be recovered and overall yield is enhanced. In the embodiment illustrated in FIG. 2, the places where a waste stream can be reinserted into the treatment system include: the inlet to heat exchanger 38 or conduit 45; the outlet of heat exchanger 38 or conduit 46; in the lower flash tank at 44; or in stripping vessel 30 or conduit 47. In the alternative embodiment illustrated in FIG. 3, the waste stream can be reinserted at the inlet to heat exchanger 76 or conduit 88, the outlet of heat exchanger 76 or conduit 90, or in lower flash tank section 74 at 86. In either embodiment, it is preferred to insert the waste stream in the lower flash tank or the outlet of the heat exchanger.

Although the sulfur-bearing residue treatment system of the present invention can be used in a single manufacturing process to treat the sulfur-bearing residues generated by that one process, it is also contemplated within the present invention to route other sulfur-bearing residue streams generated by other processes to this sulfur-bearing residue treatment system. The feeds from these other processes may be commingled if the components of the streams are compatible, or separated if the components in the residue streams are not compatible. If blended, the streams can be blended at the inlet or the outlet. Diluents and/or dispersants may be added when needed to facilitate pumping of any residue streams to the residue treatment system. Suitable diluents include acetic acid, oil, sulfuric acid, acid residue (before or after concentration), methanol, acetone and other recoverable organic liquids. Suitable dispersants comprise organic polymer, ammonium salt, water, and ethylene glycol.

Another aspect of the present invention is that another vessel containing a vacuum could be used to further concentrate the concentrated residue after it exits the stripping vessel or the lower flash tank if desired. The vacuum serves to facilitate the removal of more water in the residue stream. Also, an additional heat source could be used in conjunction with the vacuum to remove even more water from the residue stream. This would be desirable if the concentrated residue is to be sent to an acid regeneration process, a disposal process, or ammonium sulfate process because there would be a smaller volume of concentrated residue to process or dispose of as discussed above. Furthermore, the upper flash tank could incorporate a vacuum as well, if desirable; however, there is a tradeoff between the utility of using such a vacuum and the resultant increase in equipment size for those flash tanks. Utilizing a vacuum in these flash tanks would be desirable where some component of the sulfur-bearing residue stream would not tolerate high temperatures. Although the present invention has been described in detail, it should be understood that various changes, substitutions and alterations can be made hereto without departing from the spirit and scope of the invention as defined by the appended claims.

What is claimed is:

1. A process for stripping organics from a sulfur-bearing residue stream comprising:
   a) conveying a sulfur-bearing upper flash zone feedstream to an upper flash zone; and flash vaporizing the sulfur-bearing upper flash zone feedstream to form an overhead organics and water stream, and a liquid, organics-containing, sulfur-bearing residue stream;
   b) conveying the liquid, organics-containing, sulfur-bearing residue stream to a stripping zone; and
   c) in the stripping zone, stripping the liquid, organics-containing, sulfur-bearing residue stream consisting of indirectly heating the liquid, organics-containing, sulfur-bearing residue stream to form a vapor stream containing organics and a liquid residue stream.

2. The process according to claim 1 further comprising condensing the vapor stream.

3. The process according to claim 1 wherein the liquid, organics-containing sulfur-bearing residue stream is provided continuously to the stripping zone.

4. The process according to claim 1 further comprising adding a waste stream to the stripping zone.

5. The process according to claim 1 further comprising condensing the overhead organics and water stream.

6. The process according to claim 1 wherein the indirect heating is effected at a pressure not greater than atmospheric.

7. The process according to claim 1 wherein the indirect heating is effected by irradiating at least a portion of the stripping zone with microwave energy.

8. The process according to claim 1 further comprising adding a reactant to the stripping zone, said reactants being capable of reacting with said organics to convert said organics to organic compounds which are more volatile than said organics.

9. A process for stripping organics from a sulfur-bearing residue stream comprising:
   a) conveying a liquid, organics-containing, sulfur-bearing residue stream to a stripping zone,
   b) stripping the liquid, organics-containing, sulfur-bearing residue stream, in the stripping zone, to form a vapor stream containing organics and a liquid residue stream,
   c) conveying the liquid residue stream to a lower flash zone, and
   d) indirectly heating the contents of the lower flash zone to flash vaporize the contents of the lower flash zone into a lower flash zone vapor stream and a lower flash zone liquid residue stream.

10. The process according to claim 9 wherein the liquid, organics-containing, sulfur-bearing residue stream is provided by conveying a sulfur-bearing upper flash zone feedstream to an upper flash zone; and flash vaporizing the sulfur-bearing upper flash zone feedstream to form an overhead vapor organics and water stream, and a liquid, organics-containing, sulfur-bearing residue stream.

11. The process according to claim 9 wherein the lower flash zone residue stream is further subjected to a reduced pressure as compared to the lower flash zone.

12. The process according to claim 9 further comprising conveying the lower flash tank vapor stream to the stripping zone.

13. The process according to claim 9 further comprising condensing the stripping zone vapor stream.

14. The process according to claim 9 further comprising adding a waste stream to the lower flash zone or the stripping zone.

15. The process according to claim 9 further comprising adding an alkanol to the lower flash zone.

16. A process for stripping organics from a sulfur-bearing residue stream comprising:
   (a) conveying a liquid, organics-containing, sulfur-bearing residue stream to a stripping zone;
   (b) in the stripping zone, stripping the liquid, organics-containing, sulfur-bearing residue stream to form a vapor stream containing organics and a liquid residue stream;
   (c) conveying the liquid residue stream to a lower flash zone;
   (d) in the lower flash zone, flash vaporizing the liquid residue stream into a lower flash zone vapor stream and a lower flash zone liquid residue stream;
   (e) withdrawing the lower flash zone liquid residue stream from the lower flash zone and separating the lower flash zone liquid residue stream into a first portion and a second portion; and
   (f) indirectly heating the first portion of the lower flash zone liquid residue stream and returning the heated first portion of the lower flash zone liquid residue stream to the lower flash zone.

17. The process according to claim 16, wherein the liquid, organics-containing, sulfur bearing residue stream is provided by conveying a sulfur-bearing upper flash zone feedstream to an upper flash zone; and flash vaporizing the sulfur-bearing upper flash zone feedstream to form an overhead vapor organics and water stream, and a liquid, organics-containing, sulfur-bearing residue stream.

18. The process according to claim 16, wherein the second portion of the lower flash zone liquid residue stream is further subjected to a reduced pressure as compared to the lower flash zone.

19. The process according to claim 16, further comprising conveying the lower flash zone vapor stream to the stripping zone.

20. The process according to claim 16, further comprising condensing the stripping zone vapor stream.

21. The process according to claim 16, further comprising adding a waste stream to the lower flash zone or the stripping zone.

22. The process according to claim 16, further comprising adding an alkanol to the lower flash zone.

* * * * *